(12) United States Patent
Bauer et al.

(10) Patent No.: US 11,331,419 B2
(45) Date of Patent: May 17, 2022

(54) SYSTEM FOR OPTIMIZING PUMPING SESSION SUCCESS

(71) Applicant: MEDELA HOLDING AG, Baar (CH)

(72) Inventors: Ryan Bauer, Fox River Grove, IL (US); Brian H. Silver, Woodstock, IL (US)

(73) Assignee: MEDELA HOLDING AG, Baar (CH)

( * ) Notice: Subject to any disclaimer, the term of this patent is extended or adjusted under 35 U.S.C. 154(b) by 690 days.

(21) Appl. No.: 15/952,800

(22) Filed: Apr. 13, 2018

(65) Prior Publication Data

US 2019/0314562 A1 Oct. 17, 2019

(51) Int. Cl.
*A61M 1/06* (2006.01)
*G16H 40/63* (2018.01)
*G05B 13/02* (2006.01)

(52) U.S. Cl.
CPC ........... *A61M 1/062* (2014.02); *G05B 13/024* (2013.01); *G16H 40/63* (2018.01); *A61M 2205/3334* (2013.01); *A61M 2205/3584* (2013.01); *A61M 2205/50* (2013.01); *A61M 2205/502* (2013.01); *A61M 2205/52* (2013.01); *A61M 2205/581* (2013.01)

(58) Field of Classification Search
CPC .......... A61M 1/062; A61M 2205/3334; A61M 2205/3584; A61M 2205/50; A61M 2205/502; A61M 2205/52; A61M 2205/581; G05B 13/024; G16H 40/63; G16H 10/60; G16H 10/06
See application file for complete search history.

(56) References Cited

U.S. PATENT DOCUMENTS 8,597,234 B2 12/2013 Larsson
2016/0224611 A1* 8/2016 Pfenniger ........... G06F 16/2365

FOREIGN PATENT DOCUMENTS

WO WO-2017139437 A1 * 8/2017 .......... A61M 1/0031

* cited by examiner

*Primary Examiner* — Brandy S Lee
(74) *Attorney, Agent, or Firm* — McDonnell Boehnen Hulbert & Berghoff

(57) ABSTRACT

A system for improving a breastpumping session is disclosed. The system includes a database having at least one data group, the database being configured to send and receive group data regarding a pumping pattern. The system also includes at least one data processing unit configured to analyze pumping data regarding the breastpumping session and compare the pumping data to the group data. Further, the system includes at least one breast pump system communicably coupled to the data processing unit. Real-time changes to the breastpumping session are implemented to the breast pump system based on the analysis of the pumping data.

16 Claims, 2 Drawing Sheets

SYSTEM FOR OPTIMIZING PUMPING SESSION SUCCESS

TECHNICAL FIELD

The present disclosure relates to a system for optimizing success during a breast pumping session.

BACKGROUND

Breast pumping with a breast pump device to extract breast milk can be a challenging experience for mothers. One challenge arises from the fact that mothers do not necessarily know when they experience a Milk Ejection Reflex (MER) while using a breast pump device.

U.S. Pat. No. 8,597,234 to Larsson, which is incorporated by reference herein in its entirety, discusses an improvement to a breast pump device where the use of sensors in connection with breast pumping enable the understanding of the process of milk letdown and expression, as well as provide a signal or data in a control function, e.g., to a breast pump capable of analyzing the sensor data and making adaptations in operation in reaction to the data/signal. A device is adapted to receive output signals from the one or more sensors. An instrument for monitoring the output of the sensing devices can also be provided. The patent further discusses that other sensors may also be employed to study other phenomenon associated with breast pumping.

The ability to automatically operate changes between modes in breast pumping based on sensor data is not the only improvement that could assist mothers with breast pumping. For example, data from mothers having a common MER pattern could be correlated and used to optimize the function of pumps connectable to a system for optimizing guide values as discussed, for example, in US 2016/0224611, which is incorporated by reference herein in its entirety.

Additionally, recent studies have looked at the effect of journaling of breast pumping information. One study indicates that an increased awareness in pumping frequency can lead to an increase in breast milk feedings for NICU babies.

Some known systems seek to improve an individual mother's breast pumping experience by offering her a variety of information related to her breast pumping session. However, the mother is still left with the need to call an expert or resort to research to try and find a solution to a problem that arises during a pumping session based on inadequacies of the known systems directed solely to the individual outcome of a pumping session.

SUMMARY

One aspect of the disclosure is a system for improving a breast pumping session is disclosed. The system includes a database having at least one data group, the database being configured to send and receive group data regarding a pumping pattern, at least one data processing unit configured to analyze pumping data regarding the breast pumping session and compare the pumping data to the group data, and at least one breast pump system communicably coupled to the data processing unit and configured to implement real-time changes to the breast pumping session of the breast pump system based on the analysis of the pumping data.

In another aspect, a method for improving a breast pumping session using the system is disclosed. The method includes receiving, via the at least one data processing unit, the pumping data regarding the breast pumping session from the breast pump system, analyzing, via the at least one data processing unit, the pumping data and comparing the pumping data to the group data, and sending, via the at least one data processing unit, a message to the breast pump system based on the analysis of the pumping data and thereby causing implementation of real-time changes to the breast pumping session.

In yet another aspect, a system for improving a breast pumping session includes a database having at least one data pumping session, the database being configured to send and receive group data regarding a pumping pattern, at least one data processing unit configured to analyze pumping data regarding the breast pumping session, the data processing unit being communicably coupled a computing device, the computing device having a user interface, and at least one breast pump system communicably coupled to the data processing unit. The computing device is configured to request and receive feedback from a user of the breast pump system during the breast pumping session via the user interface, and the breast pump system is configured to implement real-time changes to the breast pumping session based on the user feedback received by the user interface of the computing device.

In yet another embodiment, a breast pump system is disclosed. The breast pump system includes at least one breastshield having a portion within which a woman's breast is received for the expression of milk, a source of pressure in communication with the at least one breastshield, and a controller configured to execute a pumping pattern for a breast pumping session. The controller is further configured to send pumping data to a data processing unit for analysis and receive the analyzed pumping data from the data processing unit, and the controller is configured to modify the pumping pattern in real-time based on the analyzed pumping data.

BRIEF DESCRIPTION OF THE FIGURES

The accompanying drawings are included to provide a further understanding of the methods and devices of the disclosure, and are incorporated in and constitute a part of this specification. The drawings are not necessarily to scale, and sizes of various elements may be distorted for clarity. The drawings illustrate one or more embodiment(s) of the disclosure, and together with the description serve to explain the principles and operation of the disclosure.

DETAILED DESCRIPTION

In accordance with the principles herein, a connected system shown generally at 100 that provides pumping patterns directed to optimizing a mother's success during a milk pumping session is set forth. The system can present the mother with patterns that can be selected and used during various modes of operation of a breast pump system 110, where patterns for various modes of operation are derived from an analysis of data and feedback received from the mother's breast pump 110 and/or other connected pumps of the system operated by mothers having a common data group. For example, preferred patterns of mothers of a particular group can lead to the availability of optimized patterns for various modes of operation that can be derived from the data group system data. Further, mothers can be classified in groups based on a commonality such as MER pattern, illness, hospital stay of the mother or baby, fussy baby, or any other suitable group.

Figure 1:
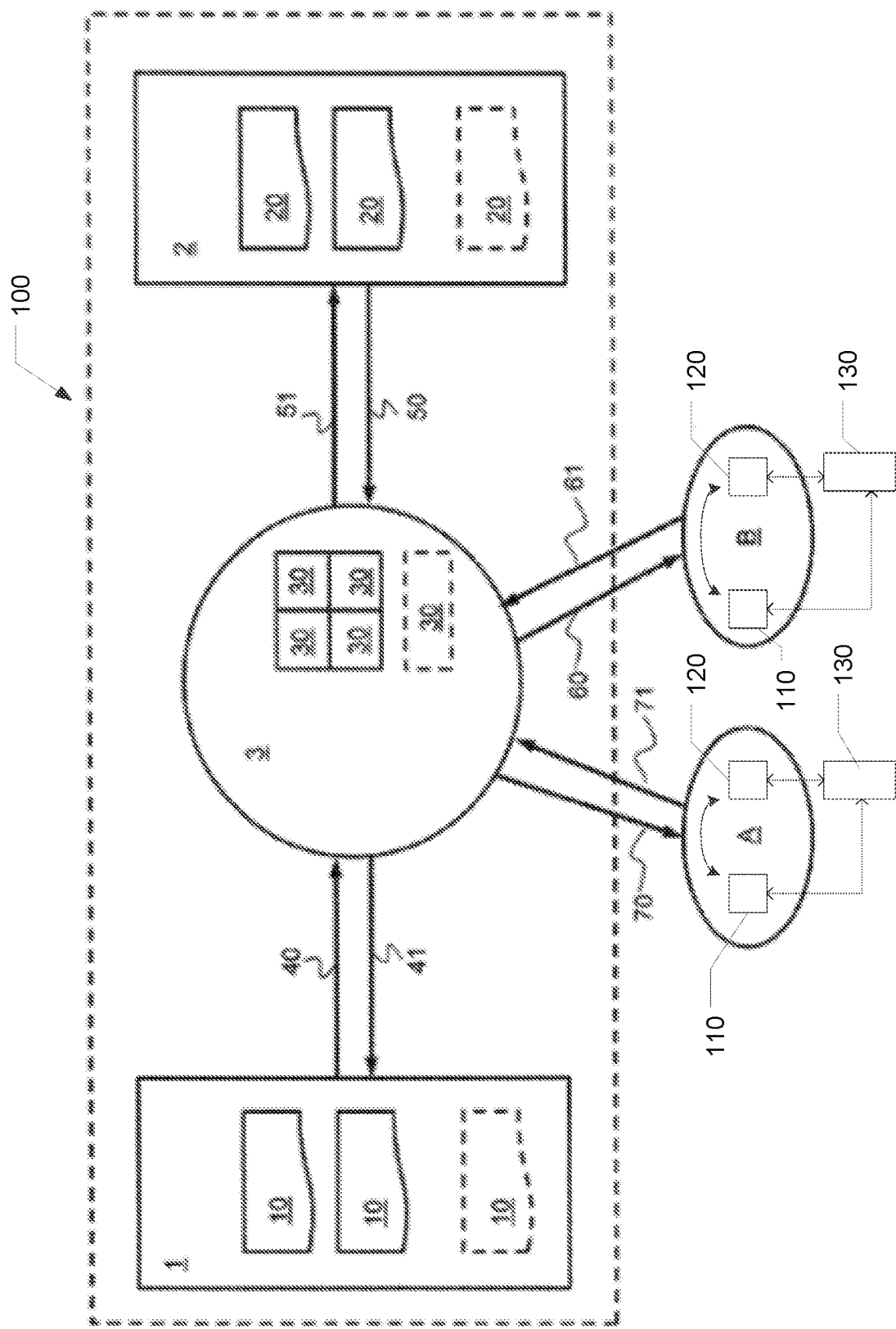
FIG. 1 illustrates a system constructed in accordance with one embodiment of the disclosure.

Referring to FIG. 1, reference numeral 1 denotes a first data set or database and reference numeral 2 denotes a second data set or database. In some embodiments, additional data sets may also be present.

Each data set 1, 2 comprises at least one, but shown in FIG. 1 as two or more data groups 10, 20. Each data group is assigned to an external target group A, B. The at least two data sets 1, 2 are connected to a data processing unit 3. In the data processing unit, guide values 30 are generated or stored therein. Data is transferred from the first and second data sets 1, 2 into the data processing unit 3. The arrows 60, 70 respectively show a first and a second guide value output to a first and second target group A, B, more precisely to an individual who fits into this target group. The arrows 61, 71 respectively show a first and a second transfer of new data which are returned from the target group A, B, more precisely from the corresponding individual, into the system, that is to say into the data processing unit 3. The arrows 41, 51 respectively show a first and a second conversion of the first and second data sets 1, 2 in accordance with the data processing unit 3 on the basis of the new data received.

US 2016/0224611 provides a structure for improving operation of systems that include a device from a manufacturer based on data received and weighted by the system from devices or users in a data group. In order to further enhance and optimize the experience for the mother, feedback from the mother can be derived, based on sensor output, or direct feedback from the mother, that can further optimize her individual pumping session due to her connection with the system. In this manner, the mother has the opportunity to use the best available recommended pattern from the overall structure of the system, while augmenting the result based on her individual experience without necessarily having to consult an expert during the session.

Additional benefit to the outcome and success of each individual of a data group during a session with a device from the manufacturer can be improved by suggesting or making immediate changes to the device that can optimize a current session while the session is underway based on sensor data and or feedback, in view of the analysis of the group data. In an embodiment, either the mother or the device can implement immediate changes in real time surrounding a breast pumping session that optimize the outcome of her session while it is underway. To this end, the breast pump device or an application or other computing device 130 can include prompts and notifications that interact with the options selected or one or more basic questions that mom can answer with any suitable input device by pushing a button, voice command, or other suitable input. The system can also provide automatic updates before or during a pumping session. Alternatively, a mother can select options to customize her session to ensure a good outcome for a particular session.

In other words, embodiments of a system constructed in accordance with the principles herein provide new ways for mothers to interact with the best available recommendations based on her data group either by merely connecting her pump to the system or by further interacting with the system.

Based on current research, there are four main letdown patterns of MER. Moms generally fall into one of the four categories of MER. Historically, new breast pumping research information was obtained from a research lab such as University of Western Australia.

Now, in accordance with the principles of the present disclosure, the system can take information from individual mothers of a data group during a pumping session, if the mother chooses to connect to the system, and can analyze and optimize the information to develop a database that will help each mother in a data group interact in an optimal way with her pumping session and deliver her optimized guides and operational parameters based on an analysis of the data group.

The information available from the system, constructed in accordance with the principles herein, can allow mothers to interact with selections or data to either optimize her goals during a breast pumping session or to help her select the best parameters for her goals or personal optimization of her usage based on interacting with her personal data in view of the group data. Each mother of a data group of the system can choose to interact with suggested parameters or libraries in the database to help guide her through a pumping session, or she can interact with the database based on her own personal data, current or historic pumping session data, while still receiving optimized patterns for her data group, depending on how the user chooses to interact with the system.

In an embodiment, a mother can operate a smart breast pump, such as the Medela Sonata® breastpump, for example. The mother can elect to connect her smart breast pump to the system and maximize her interaction with available technology relevant to optimizing her breast pumping session. The system 100 can be adapted to include components that allow the interacting function for both old technology breast pumps and new technology (smart) breast pumps.

Figure 2:
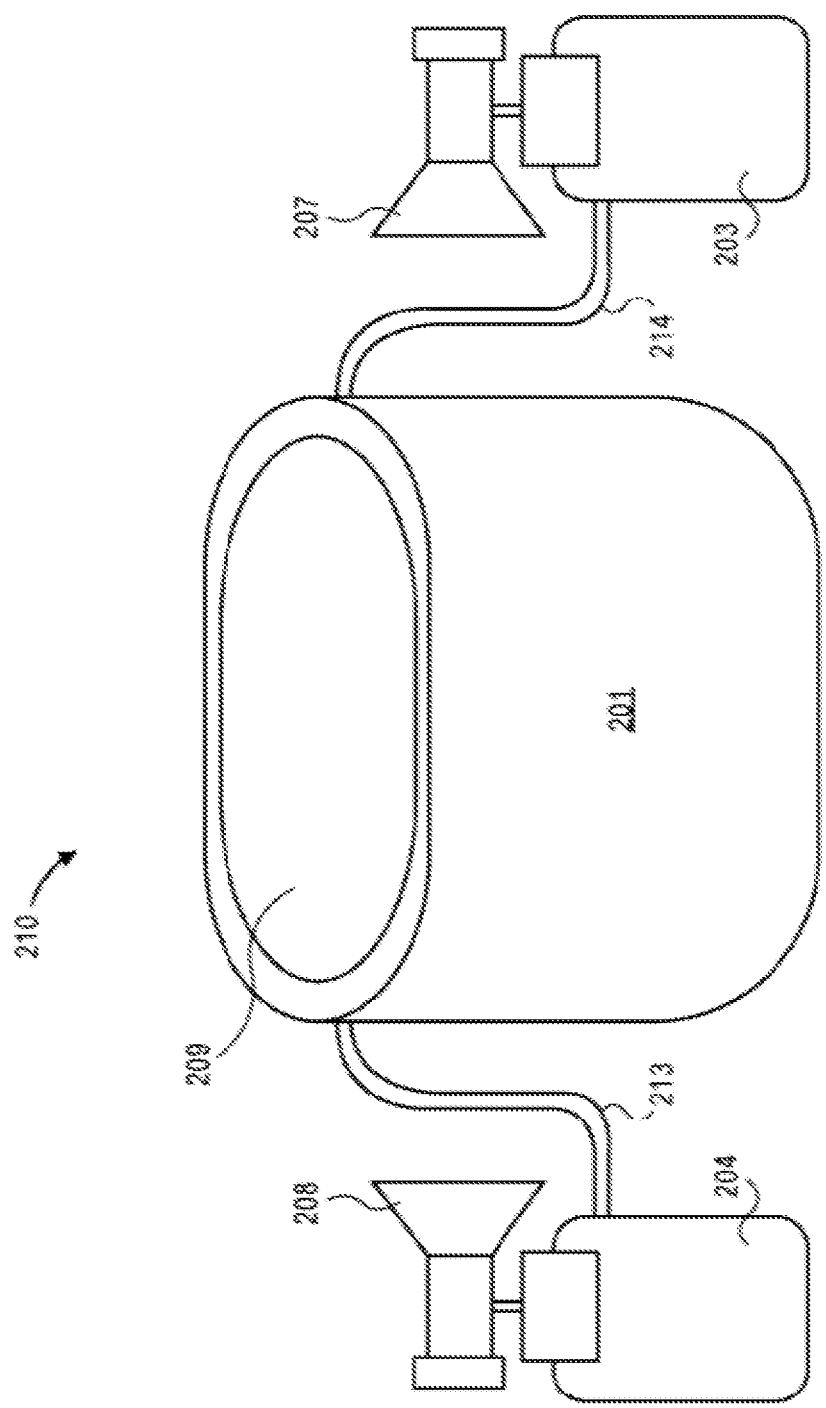
FIG. 2 shows an example breast pump system for use with an embodiment of the present disclosure.

Referring to FIG. 2, depicted is a more detailed schematic of an exemplary breastmilk expression device, or breast pump system 210. The breast pump system 210 may include a breast pump housing 201 portion as well as a "kit" or portable components. Generally, the breast pump housing 201 can house internal components such as a powering component (e.g., a motor), and a mechanism for generating pressure to extract milk (e.g., a piston within a cylinder or other suitable mechanism). The housing can also incorporate various external components, such as a user interface 209, a plug or other interface to a power source, and a set of batteries or battery pack that can be connected externally or internally, if desired. Further, the kit may include a set of breastshields 207, 208, a set of bottles 203, 204, tubing components 213, 214, as well as other components not depicted in FIG. 2 including membranes, diaphragms, valves, and/or the like. In some embodiments, the breast pump system 210 further includes a controller (not shown) configured to execute a pumping pattern for a breast pumping session. In some embodiments, the controller is further configured to send pumping data to the data processing unit 3 for analysis, and receive the analyzed pumping data from the data processing unit. In some embodiments, the controller is configured to modify the pumping pattern of the breast pump system in real-time based on the analyzed pumping data. It should be appreciated that additional or alternative components for the breast pump housing 201 and the kit of the breast pump system 210 are envisioned.

Referring again to FIG. 1, if a mother chooses to interact with a given database of the system, she can use either old or new technology breast pumps with the addition of a sensing device 120. For example, the system can include a flow sensor, or other suitable sensing device 120, and the user can benefit from interacting with a database of the system based on her personal data derived using the sensor technology during a pumping session.

Alternatively, a user can interact with a collected database for a data group as a guide to obtain information or suggestions for various recommendations or problems that may arise during her session, based on her data group, without sending her own data during the course of a pumping session. In addition, a mother can input data from her observations during a particular pumping session into an application connectable to the database, or directly into the system.

In an embodiment, an application can be associated with the system to facilitate a mother's interaction with the system. The application can be available on a computing device, tablet or smartphone, or other suitable device that not only detects or receives data relating to changes during the mothers pumping session but also selectively and operably connects to the system to provide updates to the mother and/or mother's breast pump from the database of the system.

The application can continuously or intermittently determine if a new action should be taken to modify choices of the mother or settings of the pump based on input derived during a live pumping session to optimize and guide the mother through the pumping session.

In accordance with the principles herein, the system 100 can process and analyze data for very large data groups of mothers, including large amounts of data on each mother and how those variations or lack of variations occur based on environmental, pumping parameters, emotional, time of day, or other factors, while providing real time updates back to the mothers to optimize their breast pumping experience.

Further, in an embodiment the system can provide sets of data for ongoing research projects while protecting the individual health data information of the mothers in a particular data group. In an embodiment, the system can connect to a Hospital or Research facility Wi-Fi connection to facilitate the collection of data while stripping the individual health information from the data packets sent to the local server via Wi-Fi. Such data can include, for example, data that relates to breast cancer or other health condition studies. The data results could be provided to see if breast feeding reduces chances of breast cancer or other diseases for mothers.

At the same time, the system can deliver real time updates and suggestions to the members of a research data group directly so that the mothers can benefit from the updates from the system.

In accordance with the principles herein, an analysis of the data for a particular data group can identify trends that seem to fit with each other and may be contributing to or taking away from the successful outcomes of a particular data group. As a result, the system can formulate and deliver different types of therapies for issues identified as a result of comparative studies of the data from a data group.

The comparative capability of the system could also produce data that will help an associated manufacturer develop better products. Additionally, the data can help the system identify specific devices that could be most effective in addressing a particular issue the mothers of a particular data group are experiencing.

In an embodiment, the system can generate comparative data for a mother to help her see how she is doing compared to the patient population of her data group. The data groups could also be further subdivided to help identify best solutions for a particular sub group in a more efficient manner.

The system could categorize top tips for all users, users of a set of data groups, or users in a particular data group the conveys current analyzed information based on data derived from the system regarding the actions taken by the most successful users to provide a suggested model for improvement.

Further, in an embodiment the system could provide motivation for the mothers to focus on improving the quality or outcome of their breast pumping sessions by grouping the mothers into groups that can compete, or "gamify" the experience. For example, mothers in Chicago could form a data group that competes with mothers in New York. Local hospital could interact with groups formed to provide them with information regarding programs they are hosting that could further benefit the data group's chances of success with breast pumping. Alternatively badges or other rewards could be provided to the mothers to enhance their experience with the system.

Further, the system could provide graphical information for moms in a data group to show them targets to meet their output goals based on production or duration derived from information received in the database. Such information would allow the system to provide a meaningful benefit to moms during their use of the system to provide them with concrete information regarding their progress and projected success.

One important advantage of a system constructed in accordance with the principles herein is that the system can prevent mother's from pumping longer than necessary based on the MER data group and related information of the system in view of the real time data received during a particular pumping session by the system. To this end, the system can send a signal to the device to stop the device. Alternatively, the system can notify the mother using a suitable component, such as through an application on a computing or other suitable device or through her breast pump, for example, by sending out a sound notification such as a chime or by any other suitable means or device or sound.

The system can determine if it should generate and send a signal or notification to stop pumping when mom hits a certain percentage, such as 80% of her milk production, or for her to stop pumping, and mom can adjust efficiency levels. The system can also predict the quality of a mothers pumping session based on knowing her pattern and what she is doing or just based on her historical data such as the time of day or the interval since her last pumping session or breastfeed, or other data.

The system can know or approximate what will occur, then the mother can decide if she wants to change the parameters to change to more comfortable pumping or quit. The mother can also decide if she prefers to come back after a break, such as in an hour and adjust the parameters of pumping to improve her experience.

There are mothers that do not sense MER and the system can tell the mother or the pump when MER occurs. Various responses, such as changes in milk flow, can tell the mother when MER occurs and the system place a mark on a graph when MER data is received. In his manner, the system can mark each of the mother's MERS and can notify the mother or the breast pump thereof.

In addition, the system can catalog synthesis rates for moms in a data group to form a norm. By keeping track of data from the data group, the system could know an individual mothers synthesis rate. If the mother is exclusively pumping the system could tell when the mother will complete her session and how much milk she can estimate will be produced during the session based on the system data.

In another embodiment, the system removes all the complexities of a breast pumping session and only provides notifications or information related to selected data the mother has indicated she wants to receive from the system. Many mothers get comfortable with what they are doing during a pumping session. If the mother is comfortable with what she is doing but is not making optimal choices, her milk supply may begin to decrease. The system can alter settings or suggest settings to a mother in this circumstance based on analyzed system data.

The system could generate signals that light up a sensor or cause a pump to buzz or provide other indications when a session is finished. The sensor could interact directly with the pump without interfacing with an application on a computing or other suitable device. The system could also provide a notice to the mother regarding hydration or diet.

The system could confirm and generate a signal to the breast pump to store a MER pattern for a particular mother. The MER pattern stored in the pump could be used by the system to help the mother's pump and or pump and application to become predictive based on the mother's repeated patterns analyzed in light of the system data. To this end, the pump or application could infer information regarding the physiology of the mother's breast and communicate a category of physiology to the system to further refine the recommendations for the mother's pumping sessions.

In addition, mothers do not necessarily sit still while breast pumping. For example, hands free breast pumping devices, such as a Freestyle® breastpump, can allow a mother to move around during the pumping session. The system can further subdivide a data group into mothers that are resting during a pumping session or mothers that are moving during a pumping session based on information derived from the breast pump or from the mother.

In accordance with the principles herein, the need to conduct research regarding breast pumping in a special research environment, such as a research facility or hospital, is no longer the best or only option to collecting certain breast pumping data. A key measurement available with new technology allows for a system that ties pumping conditions to a mother's milk flow in a mother's environment, which can provide additional information about pumping session success under varied conditions.

Further, a system constructed in accordance with the principles herein eliminates the small number of subjects that typically participate in a research study. Now anyone who has a breast pump and is willing to share breast pumping session data can provide input for the database of the system. Categories of mothers can also develop specialized sections within the database that address specific challenges. For example, Preemie mothers versus regular mothers of well children can continuously provide new streams of data.

In an embodiment, the system is designed to receive data regarding a number of factors that can affect a mothers pumping session. For example, the data can include goals, problems, opportunities, different pumping conditions, health status and/or many other factors. The data may help identify local problems that exist, for example, in a particular region or population so that the local problems can be addressed. Products and concepts can be tailored to address needs derived from the system.

Further, information could be analyzed and gathered to assist clinicians with data norms and information problems for specific data groups. In this way the clinicians could become more informed give all based on research gathered by the system.

The system could include an assessment that could be completed through any of a number of ways, including a phone discussion, online portal, application on a smartphone or other device, or through a hospital EMR system, to name a few. During the assessment the mother can answer questions based on answers you can tell how successful she will be with breast pumping. Such research can identify moms early on that are likely to quit breast pumping. The system could advise the mother on her assessment results and suggest how to address the risk can also identify how likely mom is to have enough milk to feed her baby. The system could also provide this information based on a medical record and deliver to a hospital EMR system without knowing the private health data of the mother.

The assessment could include a variety of factors such as total time it takes her to pump; the efficiency of her pumping sessions compared to her piers; the vacuum level she chooses; if she pumps the same amount of time each time instead of waiting till all milk is drained; if she pumps on set schedule versus an irregular schedule; the time between her pumping sessions; time of the pumping sessions; any information she adds about breast feeding and total supply; total volume baby getting such as weight of her baby and/or number of diapers of baby. The system can sort information to identify high risk pumping behavior or whether the mother is supplementing with formula. The system can break the information down in terms of goal for breastfeeding duration, such as three months, six months or one year, for example. Predictive capabilities of the system can be developed based on research analysis of the system data.

In accordance with the principles herein, the system can convert old technology pumps into notification pumps that can tell mother when to push the let-down button on her breast pump or can tell the mother to increase or decrease vacuum based on a category of database information or her individual historical information, including her MER profile.

When flow dwindles down after let down the user can be notified to return the pump to stimulation mode or another pattern or vacuum level. If using a Sonata pump, the return to stimulation mode can occur automatically.

Modern breast pumps do not provide a number of different pumping patterns because it is necessary to prove and test for patterns that are efficient for the majority of moms. In accordance with the principles herein, since flow measurements are instantaneous feedback can be provided automatically allowing for real time tuning of the pump to optimize a session and milk output for a particular mother.

In accordance with the principles herein, patterns can be varied to maximize comfort while staying within vacuum range parameters based on feedback from the system. As a result, it may be possible to eliminate a switch that adjusts for vacuum. Instead, the system may be adjusted for comfort, time of session or an amount of milk desired for a session. Choices for a mother can be recorded and recommendations based on the system recommended. Selections made during a pumping session can be selected via an application on a device.

A greater number of pumping patterns can be verified in accordance with the principles herein. For example, the system may be able verify ten or twelve patterns based on the moms MER pattern and/or based on her nipple or breast tissue sensitivity. Then, the system can customize the mother's comfort choices in view of feedback confirming the physiologic response information received by the system during a pumping session. The system can provide predictive results for the mother based on her MER pattern. For example, if the mother gets very little milk output after her third let down, then the end of the session can be optimized for comfort instead of milk output.

In accordance with the principles herein, even older technology breast pumps can provide flow information during a session, when modified according to the principles herein, and with the system analyzing the derivative of the volume of milk to define a flow. When the system determines that MER has occurred, the system can inform the mother that she can now push the mode button on her breast pump.

When the milk flow changes and reduces, or mom is not getting the flow rate she wants during a session, the system can inform her and make a suggestion whether she should change the vacuum or mode of operation. Alternatively, the system could tell the mother each time she has a letdown, and if she is going to have a good pumping session or not. Further, the system can tell the mother what percentage of volume she has achieved at any given point during her pumping session.

The system could evaluate the mother's historical data to predict what is going to happen during a pumping session. Based on mom's comfort the system might be able to suggest the recommended settings for a session or could generate signals to notify her or change the settings during the pumping session.

A system constructed in accordance with the principles herein can positively influence a mother's milk flow pattern by providing feedback that will make the mother more comfortable. As a result, the system can determine an optimum pump operation and can further optimize her pumping session with information from baby nursing patterns that can be incorporated into a mother's pumping pattern.

In an embodiment, some decisions of what to inform a mother about can be based on volume, where other decisions to help with pumping information can be based on flow. For example, a notification to stop pumping can be based on either volume or number of MER's. The system can also solicit real time feedback during a pumping session. For example, the mother can be prompted to rate certain aspects of her pumping session and her response can be correlated with the pump settings. Such feedback can help determine what is most important to a mother for her session and then prompt her to select the pumping session she wants to have based on her priority, i.e. time or comfort, thus making the pump interactive. The system can gather information such as whether the mother is sore or if she recently fed, or other pertinent information to the session.

In this manner, the system can determine conditions for the mother before the pumping session begins. Flow can be monitored during the session. Feedback based on flow can be generated by the system and transmitted in real time to confirm the best settings have been selected. The system can predict the output for a session and continually update the mother with notifications based on measurement.

Other issues the mother is facing for a session can be input to the system, such as whether she is engorged. The system can then determine and generate information or signals assuring pumping parameters that address the engorgement. The system can determine if it is best to delay or more slowly change vacuum level when switching from stimulation to expression due to the mother's engorgement. In other words, the system can provide for gentler pumping until some of the milk is pumped from the breast and the pain of engorgement eases.

In addition, the system can generate a library of curves identified by system data analysis to best assist various conditions for a session. The mother can provide real time feedback if a selected curve is effective and/or comfortable for her, while the system can monitor the effectiveness based on her milk flow/volume. One or more libraries can be made available based on research or machine learning of the system.

If the mother provides feedback to the system that she is uncomfortable, the system can help determine if she is using the wrong size breastshield, or using the wrong pattern, based on machine learning.

The system can help mother's change from a Preemie Plus pattern to standard at the appropriate time. The mother can inform the system she is using a Preemie Plus pattern. The system can then automatically select Preemie Plus, or inform the mother that she has sent data for sessions where preemie plus is no longer required for her. The information provided back by the system prevents the mother from operating the breast pump in the wrong mode, and can lead to greater milk supply, longer duration of breastfeeding, and overall better outcomes for her pumping sessions.

Additionally, the system can inform the mother when she has reach lactogenisis II, or can tell her if she has delayed lactogenesis and suggest a consult with a clinician.

The system can tell a mother her collection container is full based on the data retrieved during her pumping session. The system can notify the mother or the pump to pause or stop the pump until a new container is available, or if switching containers to separate hind from fore milk. In other words, the system can customize the time to operate the pump and to pause or stop based on fullness of a collection container and either notify the mother or automatically change the breast pump system settings.

The system can store information regarding the breast pump used for a particular session, and can provide a recommendation to the mother if she is not doing well by using a particular breast pump. The system can automatically connect to a labeler or printer to print out information related to the expressed output such as volume, date, or other clinical information.

The system can identify how to improve a basil rate of milk production for mom can make suggestions for improving milk production.

An exemplary method constructed in accordance with the principles herein can include the following steps: a breast pump system is connected to a sending/receiving device; and the sending/receiving device receives or sends at least one of notifications and bidirectional information and/or operational settings from the system. The system can be adapted to interact with the user during a pumping session. Alternatively, the system can provide updated information in response to a user query that can help optimize a pumping session. In this instance, the user is not required to interact with the system, but can use the connection to obtain the latest information relevant to her pumping session from the system.

While exemplary embodiments of the present disclosure are provided herein, various changes and modifications can be made without departing from the spirit and scope of the invention. The scope of the invention is indicated in the appended claims, and all changes that come within the meaning and range of equivalents are intended to be embraced therein. For example, variations in the forming and/or any other features described in the present disclosure are within the spirit and meaning of the appended claims.

The invention claimed is:

1. A system for improving a breast pumping session comprising:

a database having a plurality of data groups, wherein each data group of the plurality of data groups has a corresponding pumping pattern;
a data processing unit configured to analyze pumping data regarding the breast pumping session, identify a data group corresponding to the pumping data, and transmit the pumping pattern corresponding to the identified data group during the breast pumping session;
a breast pump system communicably coupled to the data processing unit and configured to receive the pumping pattern from the data processing unit and implement the pumping pattern during the breast pumping session based on the determination that the pumping data corresponds with the identified data group.

2. The system of claim 1 wherein the data processing unit is configured to cause the database to update the at least one data group based on the analysis of the pumping data.

3. The system of claim 1 wherein the data processing unit is configured to provide automatic updates to the breast pump system before or during the pumping session.

4. The system of claim 1 wherein the group data is continuously updated by the data processing unit based on feedback from users.

5. The system of claim 1 wherein an application connectable to the database is associated with the system.

6. The system of claim 5 wherein the application is stored on a computing device, wherein the application continuously or intermittently determines whether an action should be taken by the user, and wherein the action comprises modifying settings of the breast pump system.

7. The system of claim 1 wherein the data processing unit sends a signal to the breast pump system to stop the breast pump system, wherein the signal is sent through an application.

8. The system of claim 1 wherein the at least one data processing unit generates predictive capabilities based on analysis of the pumping data.

9. The system of claim 1 wherein the data processing unit analyzes historical data of the user to predict results of the breast pumping session.

10. The system of claim 1 wherein the data processing unit provides recommended settings for the breast pump system to the user based on the analysis of the pumping data.

11. A method for improving a breast pumping session using the system of claim 1, the method comprising:

receiving, via the at least one data processing unit, the pumping data regarding the breast pumping session from the breast pump system;
identifying, via the at least one data processing unit, a data group among a plurality of data groups corresponding to the pumping data, wherein each data group of the plurality of data groups has a corresponding pumping pattern; and
sending, via the at least one data processing unit, a message to the breast pump system based on the analysis of the pumping data and thereby causing real-time implementation of the pumping pattern corresponding to the identified data group during the breast pumping session.

12. A breast pump system comprising:
at least one breastshield having a portion within which a woman's breast is received for the expression of milk;
a source of pressure in communication with the at least one breastshield; and
a controller configured to execute a pumping pattern for a breast pumping session, wherein the controller is further configured to send pumping data to a data processing unit for analysis, wherein the data processing unit is configured to analyze the pumping data regarding the breast pumping session, identify a data group corresponding to the pumping data, and transmit the pumping pattern corresponding to the identified data group to the breast pump system, and wherein the breast pump system is configured to receive the identified pumping pattern from the data processing unit;
wherein the controller is configured to implement the pumping pattern during the breast pumping session based on the analyzed pumping data.

13. The breast pump system of claim 12 further comprising a sensing device configured to receive pumping data from the user and transmit the pumping data to the data processing unit.

14. The breast pump system of claim 13 wherein the sensing device is located on or in communication with the breastshield.

15. The breast pump system of claim 14 further comprising a breast pump housing within which the source of pressure and the controller are positioned.

16. The breast pump system of claim 15 further comprising a collection container releasably secured to the breastshield.

* * * * *